United States Patent
Mills

(10) Patent No.: US 9,892,219 B2
(45) Date of Patent: Feb. 13, 2018

(54) USING FRACTURE MECHANISM MAPS TO PREDICT TIME-DEPENDENT CRACK GROWTH BEHAVIOR UNDER DWELL CONDITIONS

(71) Applicant: Rolls-Royce Corporation, Indianapolis, IN (US)

(72) Inventor: David E. Mills, Greenwood, IN (US)

(73) Assignee: Rolls-Royce Corporation, Indianapolis, IN (US)

(*) Notice: Subject to any disclaimer, the term of this patent is extended or adjusted under 35 U.S.C. 154(b) by 752 days.

(21) Appl. No.: 14/471,654

(22) Filed: Aug. 28, 2014

(65) Prior Publication Data

US 2015/0213166 A1 Jul. 30, 2015

Related U.S. Application Data

(60) Provisional application No. 61/932,405, filed on Jan. 28, 2014.

(51) Int. Cl.
*G06F 17/10* (2006.01)
*G06F 17/50* (2006.01)
*G01N 33/20* (2006.01)

(52) U.S. Cl.
CPC ......... *G06F 17/5018* (2013.01); *G01N 33/20* (2013.01); *G06F 2217/16* (2013.01)

(58) Field of Classification Search
CPC .................................................. G06F 17/5018
See application file for complete search history.

(56) References Cited

U.S. PATENT DOCUMENTS

| | | |
|---|---|---|
| 6,405,108 B1 | 6/2002 | Patel et al. |
| 6,498,978 B2 | 12/2002 | Leamy et al. |
| 6,591,182 B1 | 7/2003 | Cece et al. |
| 6,643,801 B1 | 11/2003 | Jammu et al. |
| 6,804,635 B1 | 10/2004 | Dhondt |

(Continued)

OTHER PUBLICATIONS

Hou et al., "An Evaluation of 3D Crack Growth Using ZENCRACK" (2001), pp. 1-28 [retrieved from http://www.dtic.mil/cgi-bin/GetTRDoc?Location=U2&doc=GetTRDoc.pdf&AD=ADA393143].*

(Continued)

*Primary Examiner* — Brian W Wathen
(74) *Attorney, Agent, or Firm* — Barnes & Thornburg LLP

(57) ABSTRACT

A computing system for predicting crack growth behavior includes technologies to predict a time-dependent crack growth mechanism in a manufactured component once a crack has been initiated in the component. The computing system generates one or more time-dependent fracture mechanism maps for the component and uses the fracture mechanism maps to determine a modified dwell transition temperature for the component. The system predicts a crack growth mechanism based on the modified dwell transition temperature and a mission-specific temperature to which the component may be subjected. Based on the predicted crack growth mechanism, the system can estimate the cyclic life or the remaining life of the component. The life prediction and/or other output of the system can be used to assess the component for a turbine engine application; for example, to modify the design, material selection, and/or maintenance plan for the component.

24 Claims, 4 Drawing Sheets

(56) References Cited

U.S. PATENT DOCUMENTS

| | | | |
|---|---|---|---|
| 6,909,960 B2 | 6/2005 | Volponi et al. | |
| 7,219,044 B1 | 5/2007 | Prevey et al. | |
| 7,412,320 B2 | 8/2008 | Brummel | |
| 7,702,447 B2 | 4/2010 | Volponi | |
| 8,006,544 B2 | 8/2011 | Holmes et al. | |
| 8,155,820 B2 | 4/2012 | Eklund et al. | |
| 8,291,589 B2 | 10/2012 | Davis et al. | |
| 8,417,432 B2 | 4/2013 | Butler | |
| 8,505,181 B1 | 8/2013 | Brostmeyer et al. | |
| 2004/0148143 A1* | 7/2004 | Deobald | G06F 17/5018 703/2 |
| 2008/0015827 A1* | 1/2008 | Tryon, III | G06F 11/008 703/2 |
| 2008/0243457 A1 | 10/2008 | deLaneuville | |
| 2009/0276166 A1* | 11/2009 | Wang | G01M 5/0033 702/34 |
| 2009/0287458 A1* | 11/2009 | El-Wardany | B23D 43/04 703/1 |
| 2010/0153080 A1 | 6/2010 | Khan et al. | |
| 2012/0130688 A1 | 5/2012 | Jiang et al. | |
| 2013/0245879 A1 | 9/2013 | Armijo Torres et al. | |
| 2015/0227659 A1* | 8/2015 | Andersson | G05B 23/0283 703/2 |

OTHER PUBLICATIONS

Y.-T. Wu, M. P. Enright, and H. R. Millwater. "Probabilistic Methods for Design Assessment of Reliability with Inspection", AIAA Journal, vol. 40, No. 5 (2002), pp. 937-946 [retrieved from https://arc.aiaa.org/doi/abs/10.2514/2.1730].*

Shokrieh et al., "Simulation of fatigue failure in a full composite wind turbine blade" (Aug. 2006), Composite Structures, vol. 74, Issue 3, pp. 332-342 [retrieved from http://www.sciencedirect.com/science/article/pii/S0263822305001145].*

Extended European Search Report for European Application No. 14195387.7-1954, dated Jul. 3, 2015, 10 pages.

Chan et al., "A Microstructure-Based Time-Dependent Crack Growth Model for Life and Reliability Prediction of Turbopropulsion Systems", Metallurgical and Materials Transactions A, vol. 45, No. 1, Sep. 5, 2014, pp. 287-301.

Ashby et al., "Fracture-Mechanism Maps and Their Construction for FCC Metals and Alloys", Acta Metallurgica, vol. 27, May 1979, pp. 699-729.

Chan et al., "Life Prediction for Turbopropulsion Systems Under Dwell Fatigue Conditions", Journal of Engineering for Gas Turbines and Power, vol. 134, No. 12, Dec. 2012, pp. 122501-8.

Mills et al., "Time-Dependent Fracture Mechanics Considerations in Titanium 6A1-2Sn-4Zr-6Mo at Elevated Temperatures", 12 International Conference on Fracture (ICF 12), Ottawa 2009, 2009, pp. 1-9.

* cited by examiner

USING FRACTURE MECHANISM MAPS TO PREDICT TIME-DEPENDENT CRACK GROWTH BEHAVIOR UNDER DWELL CONDITIONS

This application claims priority to and the benefit of U.S. Provisional Patent Application Ser. No. 61/932,405, filed Jan. 28, 2014, which is incorporated herein by reference in its entirety.

FIELD OF THE DISCLOSURE

The present disclosure relates generally to the use of fracture mechanics in the prediction of time-dependent crack behavior. Additionally, the present disclosure relates to the prediction of transitions in time-dependent crack growth mechanisms in metal alloy components of turbine engines.

BACKGROUND

Manufactured metal alloy components, such as those that are made up of a nickel or titanium alloy, can be used to build turbine engines for aerospace, industrial, and/or marine applications. During the operation of a turbine engine, these components can be subjected to high temperatures that are introduced by combustion gasses. Elevated temperatures and/or sustained loading can cause the components to crack. The mechanism by which a crack grows after it occurs may change over time. A transgranular crack mechanism refers to a cracking pattern that cuts across the grains of the material of which the component is made. An intergranular mechanism refers to a crack growth pattern that runs between and/or around the grains of the cracked material. In typical scenarios, cracks begin to grow transgranularly. Over time, factors such as temperature and creep may cause the crack growth to transition from a transgranular to an intergranular mechanism. Creep refers to the deformation of a material over time as a result of repeated exposures to high temperatures, which occurs ahead of the crack tip. The amount of creep that results in a crack may be referred to as a critical strain value. Historically, it has been believed that component failure occurs rapidly after the crack growth behavior transitions from a transgranular to an intergranular crack growth mechanism. Component end of life calculations are currently based on this assumption.

SUMMARY

The present application discloses one or more of the features recited in the appended claims and/or the following features which, alone or in any combination, may comprise patentable subject matter.

In an example, a method for predicting time-dependent crack growth behavior in a manufactured metal alloy component having a crack includes, with at least one computing device: performing finite element modeling of the component; obtaining transition criteria from the finite element modeling; performing a fractographic evaluation of the crack in the component; creating a fracture mechanism map for the component based on the fractographic evaluation of a surface of the crack, where the fracture mechanism map indicates operating conditions under which a transgranular crack growth mechanism is predicted to occur and operating conditions under which an intergranular crack growth mechanism is predicted to occur, and where the operating conditions under which an intergranular crack growth mechanism is predicted to occur are different than the operating conditions under which a transgranular crack growth mechanism is predicted to occur; and determining, from the fracture mechanism map and the transition criteria, a modified dwell transition temperature for the component, where the modified dwell transition temperature indicates a temperature at which the crack growth behavior of the component is predicted to transition from a transgranular crack growth mechanism to an intergranular crack growth mechanism. With the modified dwell transition temperature, the method generates a life prediction for the component; and modifies one or more of: a design of the component, a material selection for the component, and a maintenance plan for the component, based on the life prediction.

The method may include obtaining data indicating a mission temperature, where the mission temperature is a temperature to which the component is predicted to be subjected during operation of a turbine engine comprising the component, comparing the mission temperature to the modified dwell transition temperature, and, based on the comparison of the mission temperature to the modified dwell transition temperature, predicting the crack growth behavior of the crack in the component.

The method may include predicting a cyclic life of the component using transgranular data if the crack growth mechanism is predicted to be transgranular. The method may include predicting a remaining life of the component using transgranular data and intergranular data if the crack growth mechanism is predicted to be intergranular. In the method, the transition criteria obtained from the finite element modeling may be a function of one or more strain parameters. In the method, the one or more strain parameters may include creep and/or elasticity. The method may include obtaining a plurality of mission-specific inputs relating to the component, wherein the mission-specific inputs comprise a mission temperature, a stress gradient, and a dwell period associated with the mission temperature and the stress gradient, and determining the modified dwell transition temperature based on the stress gradient and the dwell period.

The method may include accessing a knowledge base of modified dwell transition temperature plots, selecting one of the modified dwell transition temperature plots based on the dwell period and the stress gradient, and using the selected modified dwell transition temperature plot to determine the modified dwell transition temperature. The method may include applying a plurality of different levels of stress concentration to the component over time, fractographically evaluating the crack of the component at each of the different levels of stress concentration over time, developing a plurality of fracture mechanism maps based on the fractographic evaluation of the crack at the different levels of stress concentration over time, deriving a plurality of modified dwell transition temperatures corresponding to each of the fracture mechanism maps, and determining the modified dwell transition temperature for the component by combining the derived modified dwell transition temperatures with one or more mission-specific inputs. The method may include determining the modified dwell transition temperature by evaluating a geometry of the component. In the method, the geometry of the component may include a notch, a fillet, and/or a hole. In the method, the component may be a component of a turbine engine. In the method, the fracture mechanism map may correspond to a stress gradient of the component, and the method may include determining the modified dwell transition temperature based on the stress gradient of the component. The method may include identifying a strain parameter of the component from the finite element modeling, and using the identified strain parameter to determine the modified dwell transition temperature. In another example, a computing device includes a processor and memory having stored therein a plurality of instructions that when executed by the processor cause the computing device to perform any of the foregoing methods. In another example, one or more machine readable storage media include a plurality of instructions stored thereon that in response to being executed result in a computing device performing any of the foregoing methods.

In another example, a computing system for predicting crack growth behavior in a metal alloy component includes, embodied in one or more computer accessible storage media: a fracture map generator to generate a plurality of fracture mechanism maps for the component, where each of the fracture mechanism maps indicates, for a different stress gradient, operating conditions under which a transgranular crack growth mechanism is predicted to occur and operating conditions under which an intergranular crack growth mechanism is predicted to occur, where the operating conditions under which an intergranular crack growth mechanism is predicted to occur are different than the operating conditions under which a transgranular crack growth mechanism is predicted to occur; and a modified dwell transition temperature predictor to determine a modified dwell transition temperature for the component from the plurality of fracture mechanism maps and a plurality of component-related inputs. The computing system includes a component design, selection or maintenance system to modify one or more of: a design, a material selection, and a maintenance plan for the component based on the modified dwell transition temperature.

The computing system may include a crack growth mechanism predictor to predict a crack growth mechanism of a crack in the component based on the modified dwell transition temperature. In the computing system, the crack growth mechanism predictor may compare the modified dwell transition temperature to a mission temperature, where the mission temperature is a temperature to which the component is to be subjected during operation of a turbine engine comprising the component, and predict the crack growth mechanism based on the comparison of the modified dwell transition temperature to the mission temperature. The computing system may include a component life predictor to predict a remaining life or a cyclic life of the component based on the predicted crack growth mechanism.

In the computing system, the modified dwell transition temperature predictor may determine the modified dwell transition temperature based on a stress gradient associated with the component and a dwell period associated with the stress gradient and a mission temperature, where the mission temperature is a temperature to which the component is to be subjected during operation of a turbine engine comprising the component. In the computing system, the modified dwell transition temperature predictor may determine the modified dwell transition temperature based on a plurality of strain parameters including creep and plasticity.

The computing system may include a finite element modeling subsystem to perform finite element modeling of the component, and the computing system may determine the modified dwell transition temperature based on transition criteria obtained as a result of the finite element modeling. The computing may include a scanning electron microscopy subsystem to evaluate a fracture surface of the component, and the computing system may generate the fracture mechanism maps based on the evaluation of the fracture surface of the component.

In another example, a computing system for predicting crack growth behavior in a metal alloy component of a turbine engine under a dwell condition includes instructions embodied in one or more computer accessible storage media executable by a processor to: perform finite element modeling of the component; obtain, from the finite element modeling, a plurality of strain parameters; perform a fractographic evaluation of a fracture surface on the component; with data resulting from the fractographic evaluation, generate a time-dependent fracture mechanism map for the component, wherein the fracture mechanism map indicates, for a stress gradient associated with the component, operating conditions under which a transgranular crack growth mechanism is predicted to occur and operating conditions under which an intergranular crack growth mechanism is predicted to occur, wherein the operating conditions under which an intergranular crack growth mechanism is predicted to occur are different than the operating conditions under which a transgranular crack growth mechanism is predicted to occur; and from the fracture mechanism map, determine a modified dwell transition temperature for the component. The computing system can modify one or more of: a design, a material selection, and a maintenance plan for the component based on the modified dwell transition temperature.

In the computing system, the instructions may be executable by a processor to predict a crack growth mechanism associated with the fracture surface of the component by evaluating the modified dwell transition temperature to a temperature to which the component may be subjected during the dwell condition of the turbine engine. In the computing system, the instructions may be executable by a processor to generate a life prediction for the component by evaluating data relating to the predicted crack growth mechanism.

BRIEF DESCRIPTION OF THE DRAWINGS

This disclosure is illustrated by way of example and not by way of limitation in the accompanying figures. The figures may, alone or in combination, illustrate one or more embodiments of the disclosure. Elements illustrated in the figures are not necessarily drawn to scale. Reference labels may be repeated among the figures to indicate corresponding or analogous elements.

DETAILED DESCRIPTION OF THE DRAWINGS

Figure 1:
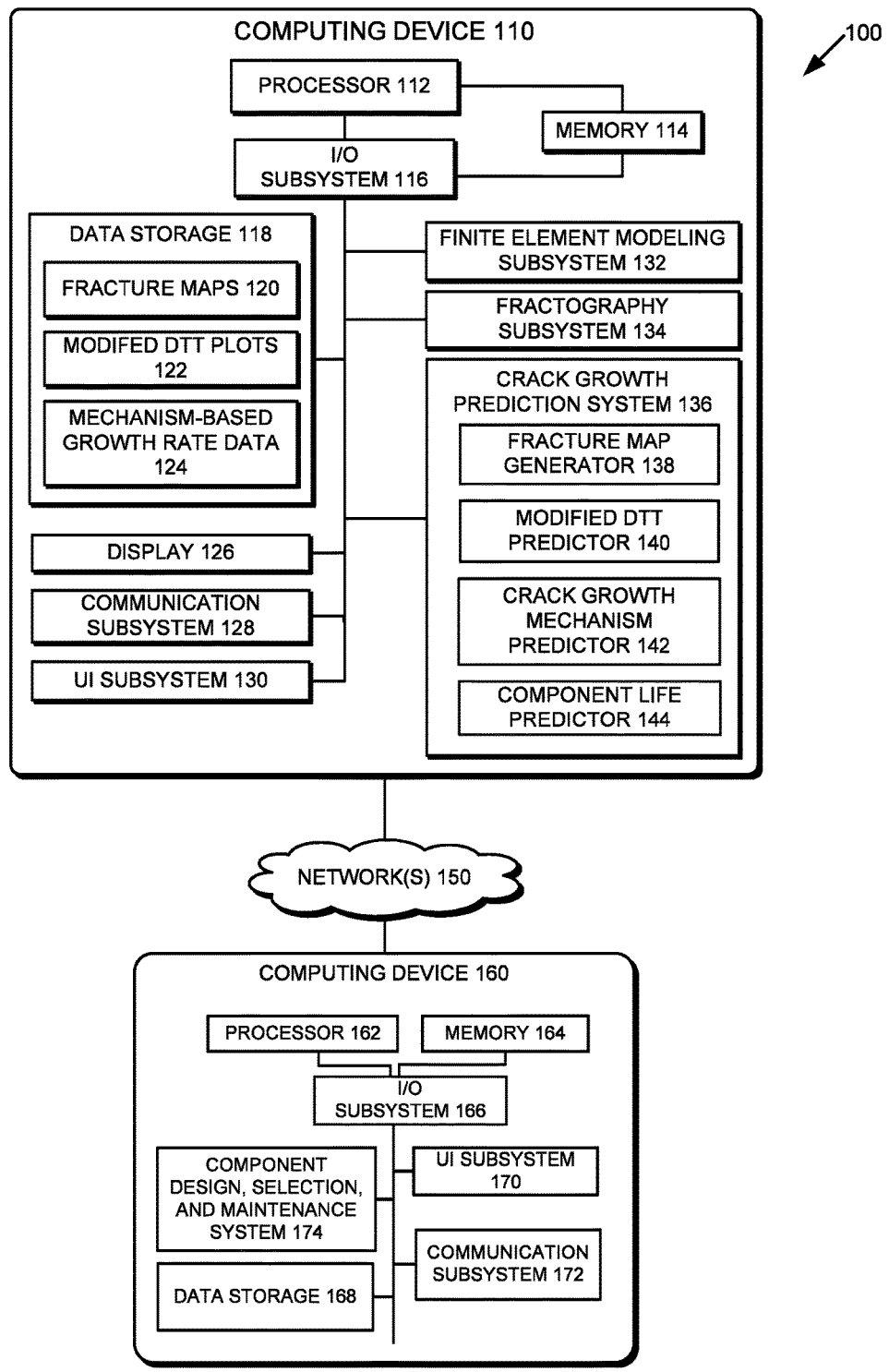
FIG. 1 is a simplified block diagram of at least one embodiment of a computing system for predicting crack growth behavior as disclosed herein.

While the concepts of the present disclosure are susceptible to various modifications and alternative forms, specific embodiments thereof are shown by way of example in the drawings and are described in detail below. It should be understood that there is no intent to limit the concepts of the present disclosure to the particular forms disclosed. On the contrary, the intent is to cover all modifications, equivalents, and alternatives consistent with the present disclosure and the appended claims.

As used herein, "dwell" may refer to, among other things, a state in which a manufactured component is subjected to a steady and elevated or uniformly increasing load and temperature for a sustained period of time. A component of the turbine engine, such as a turbine disk or a flame tube (e.g., a component located near the combustor of a turbine engine) may operate under dwell conditions during certain phases of operation of the vehicle driven by the turbine engine. For example, in an aerospace application of a turbine engine, the component may operate under dwell conditions during a climb or a cruise phase of a flight plan. A "dwell transition temperature" ("DTT") as used herein, may refer to, among other things, a temperature to which a component is subjected under dwell conditions. If the component has developed a crack, a change in the crack growth mechanism (e.g., from transgranular to intergranular) can occur when the operating temperature under dwell conditions (e.g., the "mission temperature") reaches the DTT.

Traditionally, the dwell transition temperature has been estimated based on a maximum stress intensity (Kmax), and exceeding the DTT has been assumed to be the activation point for accelerating end-of-life predictions. These existing models can be reliable if the component has, in fact, experienced a crack growth mechanism transition at the DTT. However, the inventor has observed that not all components experience the same amount of rapid crack growth rates after a dwell transition temperature has been reached. In fact, some components can operate above the traditionally-calculated DTT for a substantial amount of time before a transition in crack behavior occurs. Thus, as disclosed herein, some components can operate under a set of conditions that yields a different (e.g., higher) DTT value. The "different-than-normal" DTT determined as disclosed herein is referred to as a "modified dwell transition temperature" or "mod-DTT." Among other things, components that are determined to have a mod-DTT as disclosed herein may allow manufacturers to utilize different (e.g., lower-cost) alloys at higher temperatures and/or for longer periods of time than would normally be permitted by the existing time-dependent crack growth models.

Referring now to FIG. 1, an embodiment of a computing system 100 for predicting crack behavior in a manufactured component is shown. The illustrative computing system 100 includes at least one computing device 110, which has embodied therein a finite element modeling subsystem 132, a fractography subsystem 134, and a crack growth prediction system 136. As described in more detail below, the crack growth prediction system 136 can create one or more fracture mechanism maps for a manufactured part, such as a metal alloy component of a turbine engine, use the fracture mechanism maps to determine a modified dwell transition temperature for the part, generate a crack growth mechanism prediction for the part based on the modified dwell transition temperature, and generate a life prediction (e.g., end-of-life or cyclic life) for the part based on the crack growth mechanism prediction.

The computing device 110 includes hardware, firmware, and/or software components that are capable of performing the functions disclosed herein, including the functions of the finite element modeling subsystem 132, the fractography subsystem 134, and the crack growth prediction system 136. While not specifically shown, the computing system 100 may include other computing devices (e.g., servers, mobile computing devices, etc.), which may be in communication with each other and/or the computing device 110 via one or more communication networks, to perform one or more of the disclosed functions. The illustrative computing device 110 includes at least one processor 112 (e.g. a controller, microprocessor, microcontroller, digital signal processor, etc.), memory 114, and an input/output (I/O) subsystem 116. The computing device 110 may be embodied as any type of computing device such as a desktop computer, laptop computer, or mobile device (e.g., a tablet computer, smart phone, body-mounted device or wearable device, etc.), a server, an enterprise computer system, a network of computers, a combination of computers and other electronic devices, or other electronic devices. Although not specifically shown, it should be understood that the I/O subsystem 116 typically includes, among other things, an I/O controller, a memory controller, and one or more I/O ports. The processor 112 and the I/O subsystem 116 are communicatively coupled to the memory 114. The memory 114 may be embodied as any type of suitable computer memory device (e.g., volatile memory such as various forms of random access memory).

The I/O subsystem 116 is communicatively coupled to a number of hardware, firmware, and/or software components, including a data storage device 118, a display 126, a communication subsystem 128, a user interface subsystem 130, the finite element modeling subsystem 132, the fractography subsystem 134, and the crack growth prediction system 136. The data storage device 118 may include one or more hard drives or other suitable persistent data storage devices (e.g., flash memory, memory cards, memory sticks, and/or others). The fracture maps 120, modified DTT plots 122, and mechanism-based growth rate data 124 reside at least temporarily in the data storage device 118 and/or other data storage devices of the computing system 100 (e.g., data storage devices that are "in the cloud" or otherwise connected to the computing device 110 by a network). Portions of the finite element modeling subsystem 132, the fractography subsystem 134, and the crack growth prediction system 136 may reside at least temporarily in the data storage device 118 and/or other data storage devices that are part of the computing system 100. Portions of the fracture maps 120, the modified DTT plots 122, the mechanism-based growth rate data 124, the finite element modeling subsystem 132, the fractography subsystem 134, and/or the crack growth prediction system 136 may be copied to the memory 114 during operation of the computing device 110, for faster processing or for other reasons. The display 126 may be embodied as any suitable type of digital display device, such as a liquid crystal display (LCD), and may include a touchscreen. The illustrative display 126 is configured or selected to be capable of displaying two- and/or three-dimensional graphics, including the plots shown in FIGS. 3-4.

The communication subsystem 128 may communicatively couple the computing device 110 to other computing devices and/or systems by, for example, one or more networks 150. The network(s) 150 may be embodied as, for example, a cellular network, a local area network, a wide area network (e.g., Wi-Fi), a personal cloud, a virtual personal network (e.g., VPN), an enterprise cloud, a public cloud, an Ethernet network, and/or a public network such as the Internet. The communication subsystem 128 may, alternatively or in addition, enable shorter-range wireless communications between the computing device 110 and other computing devices, using, for example, BLUETOOTH and/or Near Field Communication (NFC) technology. Accordingly, the communication subsystem 128 may include one or more optical, wired and/or wireless network interface subsystems, cards, adapters, or other devices, as may be needed pursuant to the specifications and/or design of the particular computing device 110. The user interface subsystem 130 includes one or more user input devices (e.g., the display 126, a microphone, a touchscreen, keyboard, virtual keypad, etc.) and one or more output devices (e.g., audio speakers, LEDs, additional displays, etc.).

The communication subsystem 128 may communicate output of one or more of the finite element modeling subsystem 132, the fractography subsystem 134, and the crack growth prediction system 136 to a component design, selection, and maintenance system 174, via a network 150. For example, portions of fracture maps 120, modified dwell transition temperature plots, mechanism-based growth rate data 124, and/or component life predictions calculated as described below, may be supplied to the component design, selection, and maintenance system 174. The illustrative component design, selection, and maintenance system 174 is embodied in a computing device 160. It should be understood, however, that the component design, selection, and maintenance system 174, or portions thereof, may reside on the computing device 110 or on other computing devices, in other embodiments. The components of the computing device 160 having the same name as above-described components of the computing device 110 may be embodied similarly; therefore, the description is not repeated here.

The component design, selection, and maintenance system 174 utilizes output of the crack growth prediction system 136, such as component life predictions, in order to effectuate modifications in the design of metal alloy components, to influence component material selection, and/or to determine or modify a maintenance or end-of-life plan for the component. As such, the system 174 applies the component life predictions and other output generated by the crack growth prediction system 136 in a useful way to, for example: improve the design of a metal alloy component for a turbine engine, improve the selection of a replacement part for the component, and/or optimize the maintenance schedule or end-of-life plan for the component. While the system 174 is illustratively shown as including component design, replacement part selection, and component maintenance plan functionality, it should be understood that each of these pieces of functionality may be implemented as separate systems, in other embodiments. For example, the system 174 may be implemented as separate computer applications for component design, replacement part selection, and maintenance planning. Additionally, the different computer applications may run on different computing devices or networks with which the computing device 110 is in communication via the communication subsystem 128. Further, in accordance with this disclosure, it should be understood that many practical and useful applications of the disclosed technology are contemplated, in addition to the examples specifically mentioned herein. For example, the component life predictions and/or other output generated by the crack growth prediction system 136 can be applied to many different types of assessment processes for evaluating metal alloy components for aerospace, industrial, and/or marine applications of turbine engines.

The finite element modeling ("FEM") subsystem 132 is embodied as one or more computer-executable components and data structures for performing finite element modeling of a manufactured component, such as a metal alloy component of a turbine engine. The illustrative FEM subsystem 132 creates a mathematical model of structural characteristics of the component. For example, the finite element model created by the FEM subsystem 132 can receive component and/or mission-related inputs (such as dwell temperature, stress gradient, component geometry, grain structure properties, and/or dwell period), and solve a set of differential equations to obtain desired unknown parameters, including strain parameters such as creep and plasticity. As used herein, "stress gradient" may refer to, among other things, a mathematically-calculated data value that represents the manner or degree to which stress changes from the surface of a component to a sub-surface of the component. As used here, "component geometry" may refer to, among other things, the 2- or 3-dimensional geometric shape of a component or a portion thereof. For example, whether the component is disk-shaped or square, or whether the component includes a hole, a fillet, a square edge, a rim, or a notch is considered a feature of the component geometry. Some examples of grain structure properties are the reported sizes and orientation of regions between the material's grain boundaries, which represent the separation of crystallographic structure of the material during the material's formation. Orientation of grains and grain size is often reported by the material supplier. Grain sizes are often reported in terms of American Society for Testing and Materials (ASTM) standards. The FEM subsystem 132 may be embodied as, for example, a commercially available engineering structural analysis simulation software system such as the ANSYS system, available from ANSYS, Inc.

The illustrative fractography subsystem 134 uses fractography to study a fracture surface of the component. That is, if the component has developed a crack (e.g., as a result of stress testing or normal use), the fractography subsystem 134 creates a high-resolution digital image of the fracture surface (e.g., the crack tip and/or areas adjacent to the crack tip) that can be used to analyze the growth behavior of the crack. The fractography subsystem 134 may be embodied as, for example, a scanning electron microscope ("SEM") coupled to a software system for performing crack growth analysis of the digital image of the fracture surface. An example of a software system for performing the crack growth analysis as disclosed herein is the Design Assessment of Reliability with Inspection ("DARWIN") system developed by the Southwest Research Institute (in collaboration with Rolls Royce, Honeywell, Pratt & Witney, and General Electric).

The illustrative crack growth prediction system 136 is embodied as a number of computer-executable components and data structures, including a fracture map generator 138, a modified dwell transition temperature predictor 140, a crack growth mechanism predictor 142, and a component life predictor 144. The illustrative fracture map generator 138 interfaces with the fractography subsystem 134 to create the time-dependent fracture maps 120 as disclosed herein. The fracture map generator 138 obtains data from the fractography subsystem 134 that relates to the fractography subsystem 134's evaluation of a fracture surface of the component. For example, the fractography subsystem 134 may provide data to the fracture map generator 138 that indicates the nature, location, pattern, and/or other characteristics of the fracture surface (e.g., a surface area at or adjacent to a crack tip in the component), as well as the stress concentration level (e.g., the Kt value) at which those characteristics were observed. The fracture map generator 138 creates the fracture map 120 as a visualization (e.g., a 2-dimensional or 3-dimensional graphical representation) of the results of the fracture surface evaluation performed by the fractography subsystem 134, and stores the fracture map 120, and/or data relating thereto, in computer memory. Different fracture maps 120 are created for different levels of stress concentration that are applied to the component over time (e.g., during stress testing or normal operation under dwell conditions). Thus, each component that is evaluated by the computing system 100 may have a number of associated fracture maps 120.

Figure 3:
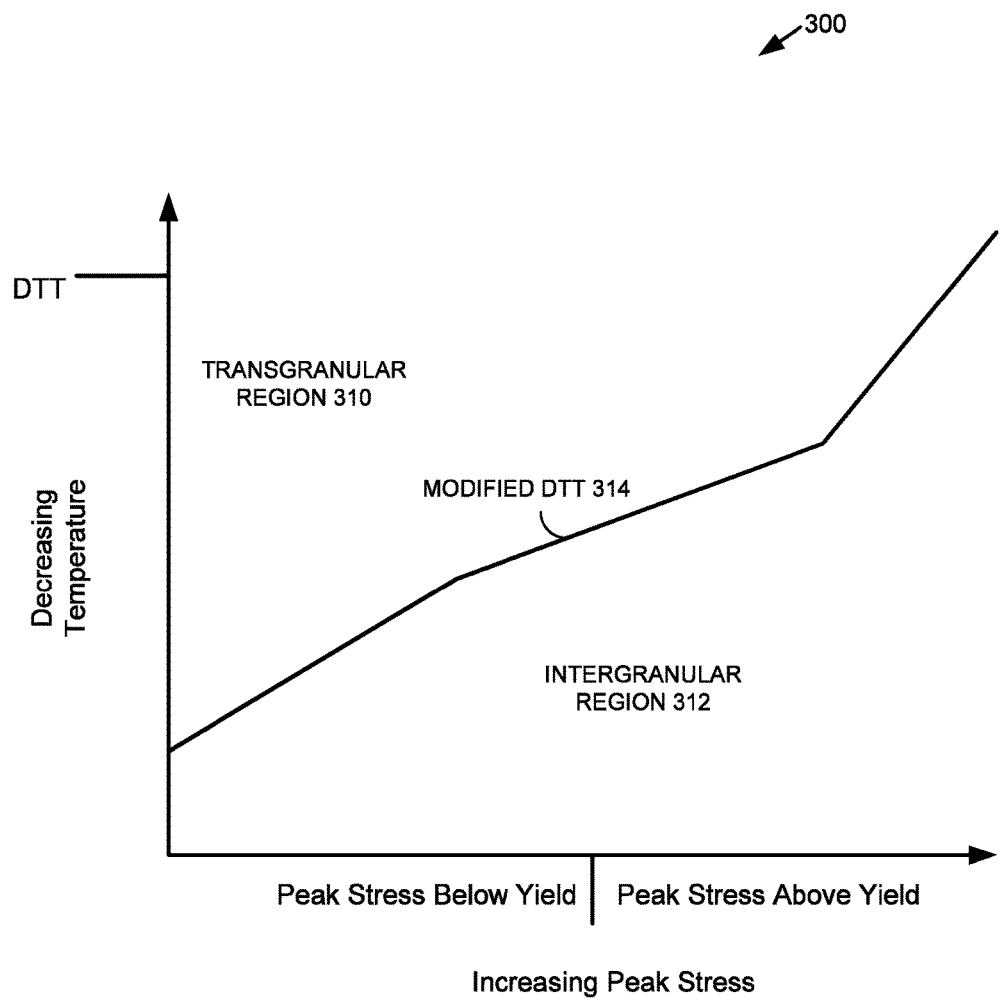
FIG. 3 is an example of a fracture mechanism map as disclosed herein.

The fracture maps 120 represent relationships between the operating temperature values (e.g., the temperature to which the component is subjected under dwell conditions) and peak stress values, over time. An example 300 of a fracture map 120 is shown in FIG. 3. Referring to FIG. 3, the fracture map 300 identifies a transgranular region 310, which includes combinations of temperature and peak stress data values that are likely to result in a transgranular crack growth mechanism. The fracture map 300 also identifies an intergranular region 312, which includes combinations of temperature and peak stress data values that are likely to result in a intergranular crack growth mechanism. A modified dwell transition temperature curve 314 indicates combinations of temperature and peak stress data values that are likely to result in a crack growth behavior transition, e.g., a transition from a transgranular crack growth mechanism to an intergranular crack growth mechanism.

The computing system 100 can be used to generate a number of different fracture maps 120 for a variety of different types of components, component geometries, stress gradients, and/or other component or mission characteristics, over time. For example, many different types of components can be observed periodically during normal use or stress testing according to different mission requirements. The various fracture maps 120 may be stored in a searchable database, knowledge base, electronic file, or other computerized data structure that can be used to store the fracture map data and data identifying the component and/or mission characteristics associated with each fracture map 120. Once such a knowledge base of fracture maps 120 is developed, the computing system 100 may be used to analyze new components without needing to create a new set of fracture maps specifically for the new component. For example, the computing system 100 may receive input (by, e.g., the user interface subsystem 130) describing one or more of the characteristics of the new component, and search the knowledge base of fracture maps 120 using the input as search criteria. The computing system can identify a fracture map 120 from the knowledge base that most closely matches the inputted search criteria, and use the matching fracture map 120 to analyze the new component.

Figure 4:
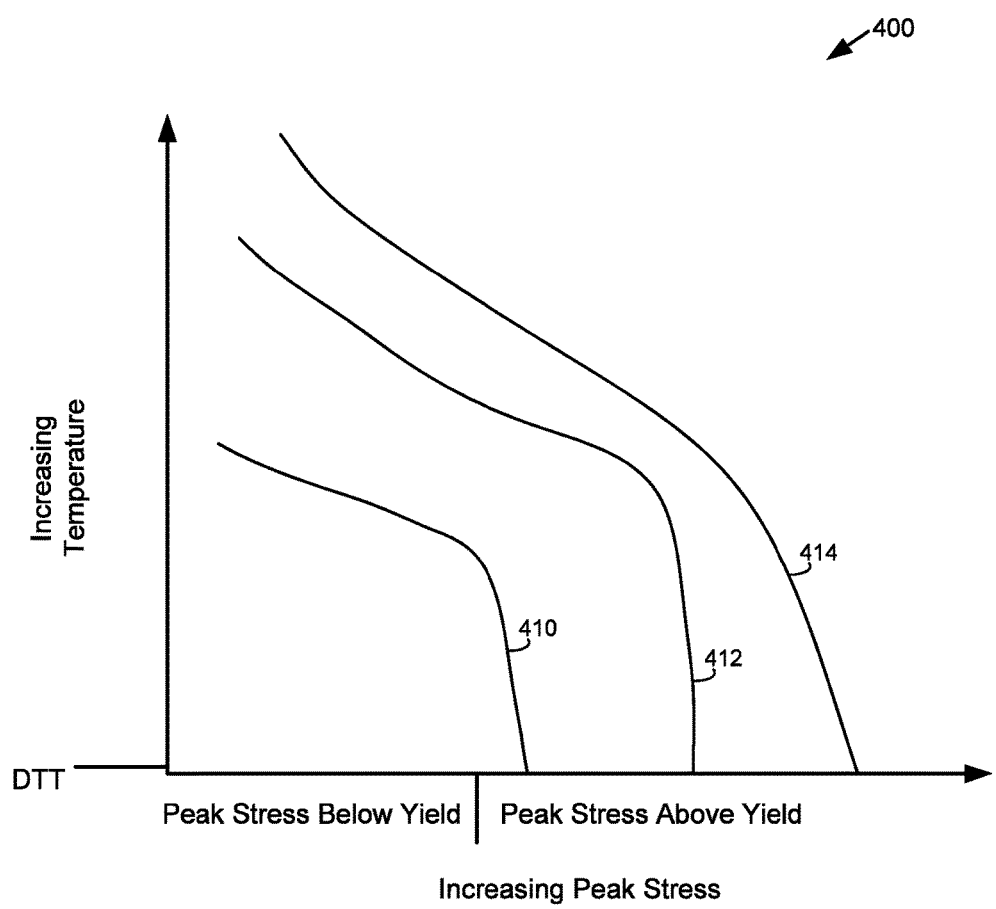
FIG. 4 is an example of a plot of modified dwell transition temperatures as disclosed herein.

The illustrative modified dwell transition temperature predictor 140 compares the crack growth behavior transition criteria obtained by the finite element modeling subsystem 132 to the time-dependent fracture mechanism maps 120 that are developed by the fracture map generator 138, to determine the modified dwell transition temperature curve that is applicable to each of the fracture maps 120. For instance, the modified DTT predictor 140 may establish a modified DTT curve (e.g., the curve 314 of FIG. 3) that corresponds to the transition criteria, for each of the fracture maps 120. The modified dwell transition temperature predictor 140 generates the modified DTT plots 122, which are embodied as 2-dimensional or 3-dimensional graphical representations of the modified DTT curves, for a number of different combinations of component and/or mission characteristics. An example 400 of a modified DTT plot is shown in FIG. 4. In FIG. 4, the curves 410, 412, 414 represent modified dwell transition temperature curves corresponding to different component and/or mission characteristics. For example, the curve 410 may correspond to a low Kt value, whereas the curve 412 may be associated with a high Kt value, and the curve 414 may be representative of a component that has notched portion (e.g., a "V-notch").

The modified DTT plots and associated component and/or mission characteristics are stored in computer memory of the computing system 100. As with the fracture maps 120, the modified DTT plots 122 may be stored in a searchable data structure so that they can be easily retrieved based on one or more search criteria, e.g., component and/or mission characteristics. Accordingly, once a searchable knowledge base of modified DTT plots 122 is created, the knowledge base can be used to match new components with appropriate modified DTT plots 122 based on component and/or mission characteristics (e.g., without having to generate a set of modified DTT plots specifically for the new component). For example, a modified DTT plot may be selected based on a comparison of the geometry of the new component to the geometries of components for which the modified DTT plots 122 have been previously generated by the computing system 100. However, some components or portions thereof have similar stress gradients even though they do not have similar geometries. For instance, the stress gradients of high-stress regions of components, such as notches, holes, and rims of disks, may be similar even though the geometries do not match. Thus, in some cases, the system 100 matches a plot 122 to a new component based on the stress gradient, alternatively or in addition to the component geometry or other factors.

To predict the modified dwell transition temperature for a particular set of component and/or mission inputs, the modified dwell transition temperature predictor 140 selects a modified DTT plot 122 in accordance with the component and/or mission inputs. The modified DTT predictor 140 determines the applicable modified DTT graphically from the selected plot 122 or by an automated comparison (e.g., by software) of the mission and/or component characteristics to the data represented by the selected plot 122.

The illustrative crack growth mechanism predictor 142 compares the modified dwell transition temperature predicted by the modified DTT predictor 140 to the actual mission temperature (e.g., the temperature to which the component is subjected under dwell conditions), and predicts the likely crack growth mechanism based on the temperature comparison. The component life predictor 144 obtains the crack growth mechanism prediction output by the crack growth mechanism predictor 142 and uses the mechanism-based growth rate data 124 and the crack growth mechanism prediction to generate a prediction relating to the life of the component. For example, if the predicted crack growth mechanism is transgranular, the component life predictor 144 may use transgranular growth rate data stored in the mechanism-based growth rate data 124 to make a prediction about the cyclic life of the component. On the other hand, if the predicted crack growth mechanism is intergranular or a mix of intergranular and transgranular, the component life predictor 144 may use both transgranular and intergranular growth rate data stored in the mechanism-based growth rate data 124, along with component life data (e.g., component life data obtained from prior testing or usage of the component) to make an end of life prediction about the component. The stored component life data may be stored in the data storage 118, and can be obtained by testing representative samples of a given material using standard testing procedures and data reduction techniques, such as (but not limited to) ASTM E647, ASTM E1457, and/or ASTM E2760.

In some embodiments, once a knowledge base of modified DTT plots 122 is established, portions of the modified DTT predictor 140, the crack growth mechanism predictor 142, and the component life predictor 144 may be executed in real time (e.g., as part of a feedback control system), to adjust the crack growth mechanism and component life predictions over time as the component and mission characteristics change, or as time elapses. For example, portions of the modified DTT predictor 140, the crack growth mechanism predictor 142, and the component life predictor 144 may be embodied in one or more executable sub-modules that can be called by another module, computer application, or process to generate the crack growth mechanism prediction and the component life prediction in response to various mission and/or component inputs or changes in those inputs, as needed over time.

Particular aspects of the methods and analyses that may be performed by the various modules of the computing device 110 may vary depending on one or more of the characteristics of the component being analyzed and/or its prescribed mission criteria. Accordingly, the examples described herein are illustrative and intended to be non-limiting. Further, the computing system 100 may include other components, sub-components, and devices not illustrated in FIG. 1 for clarity of the description. In general, the components of the computing system 100 are communicatively coupled as shown in FIG. 1 by electronic signal paths, which may be embodied as any type of wired or wireless signal paths capable of facilitating communication between the respective devices and components.

Figure 2:
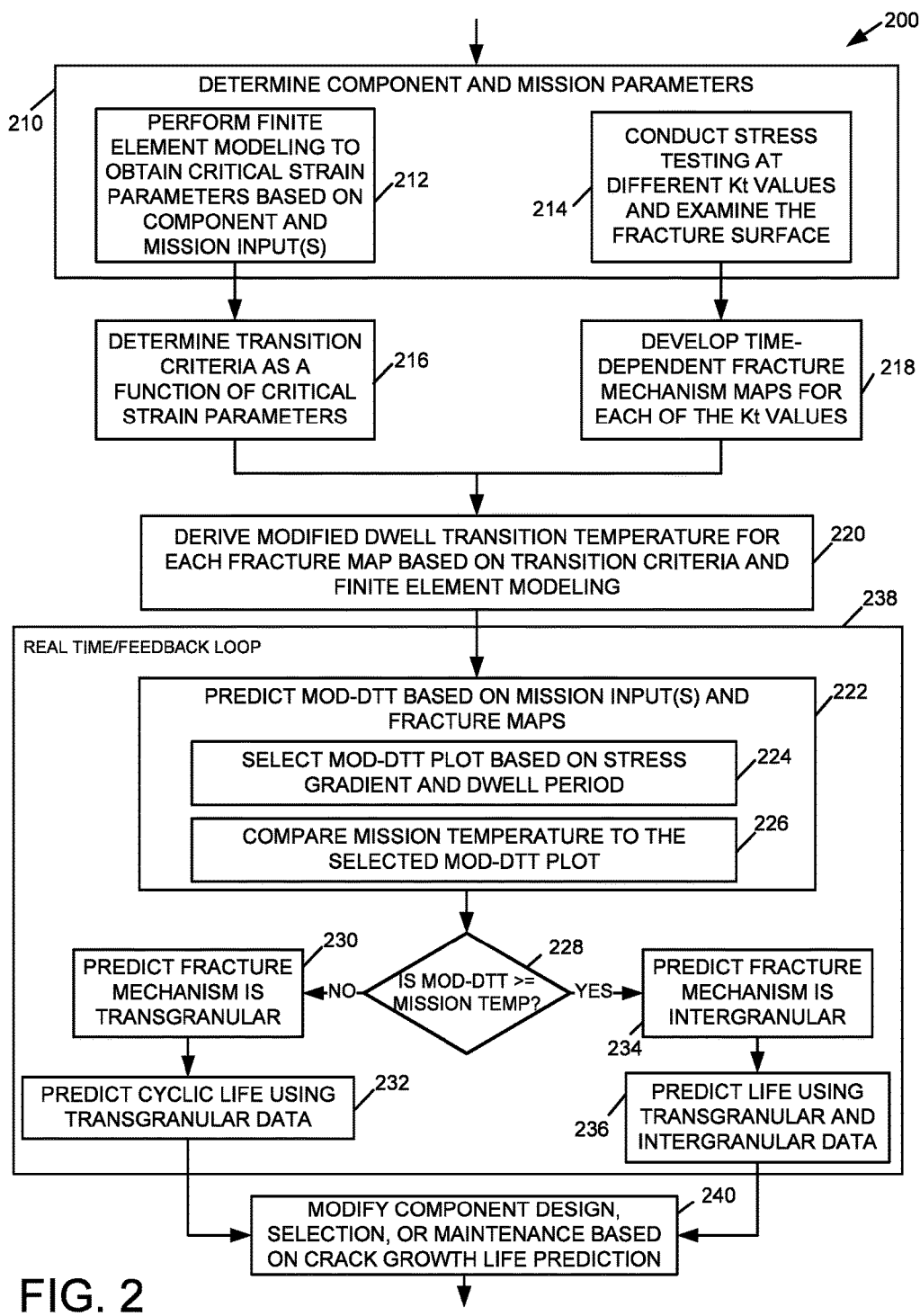
FIG. 2 is a simplified flow diagram of at least one embodiment of method for predicting crack growth behavior, which may be executed by the computing system of FIG. 1.

Referring now to FIG. 2, an illustrative method 200 for analyzing a manufactured component, such as a metal alloy component of a turbine engine, predicting time-dependent crack behavior, and predicting component life, is shown. Aspects of the method 200 may be embodied as computerized programs, routines, logic and/or instructions executed by the computing system 100, for example by one or more of the modules 132, 134, 136, 138, 140, 142, 144. At block 210, the computing system 100 determines component- and mission-related parameters for the component to be analyzed by the computing system 100. The component- and mission- related parameters may include, for example, aspects of the component design, features, geometry, and/or stress gradient, mission-specific information such as dwell temperature and/or dwell period (e.g., the time period during which the component is expected to be subjected to dwell conditions). The computing system 100 may obtain the component- and mission-related parameters by, for example, receiving user- or system-generated input via the user interface subsystem 130 and/or the communication subsystem 128. At block 212, the computing system 100 performs finite element modeling using the component- and mission-related parameters to identify the strain parameters that are considered "critical" for the particular combination of component and mission inputs. In other words, the useful strain parameters may vary from component to component and/or from mission to mission. Whereas, in the illustrative embodiments, the critical strain parameters of creep and plasticity are used, other strain parameters may be more appropriate for other types of components or missions. At block 216, the computing system 100 determines the crack growth behavior transition criteria as a function of the critical strain parameters identified at block 212. The transition criteria are data values that are mathematically calculated using the critical strain parameters and data that is dependent on the material from which the component is made. The mathematical function used to calculate the transition criteria is selected based on data trends. For example, the deformation associated with time-dependent crack growth can be described by the summation of elastic strain, plastic strain and creep strain. Given that the plastic strain and creep strain terms can accurately account for the complexities of the material's response to the geometric feature and general loading conditions, this format can predict transition accurately without further modeling complexity.

At block 214, the computing system 100 performs stress testing on the component at a number of different Kt values and examines the fracture surface (e.g., the surface of the component at or adjacent to the crack tip). To do this, the computing system 100 may perform scanning electron microscopy to obtain digital images of the microscopic structure of the fracture surface, which reveal aspects of the crack growth behavior. At block 218, the computing system 100 creates the time-dependent fracture mechanism maps 120, for each of the Kt values used in the testing performed at block 214. To do this, the computing system 100 uses software (e.g., DARWIN) to visualize the data obtained at block 214.

At block 220, the computing system 100 derives the modified dwell transition temperature for each of the fracture mechanism maps 120, based on the transition criteria obtained at block 216 and the finite element modeling performed at block 212. To do this, the computing system 100 plots, for each of the fracture maps 120, the transition criteria on the fracture map to create the modified dwell transition temperature curve (e.g., the curve 314). In other words, the computing system 100 creates the modified DTT plots 122, at block 220. At block 222, the computing system 100 predicts the component- and mission-related modified dwell transition temperature, taking into account the mission input(s) obtained at block 212 and the fracture maps 120 developed at block 218. That is, the computing system 100 generates a prediction as to the likely modified dwell transition temperature that is applicable, given the features of the component and the specific mission. To do this, the computing system 100 selects one of the modified dwell transition temperature plots (e.g., one of the plots 410, 412, 414) based on the component's stress gradient and the dwell period, at block 224. For example, the computing system 100 compares the component's stress gradient to the stress gradient for each of the Kt values that are represented on the modified DTT plots 122, and then selects one of the modified DTT plots 122 based on the dwell period obtained at block 210 as one of the mission-specific inputs. At block 226, the computing system 100 compares the mission temperature obtained at block 210 to the modified DTT plot selected at block 224.

At block 228, the computing system 100 compares the modified dwell transition temperature predicted at block 222 to the mission (e.g., dwell) temperature obtained at block 210. If the predicted modified dwell transition temperature is greater than or equal to the mission temperature, the method 200 proceeds to block 230. At block 230, the computing system 100 concludes, based on the comparison performed at block 228, that the likely current crack growth mechanism associated with the crack in the component being analyzed is a transgranular crack growth mechanism. If the predicted modified dwell transition temperature is less than the mission temperature, the method proceeds to block 234. At block 234, the computing system 100 concludes, based on the comparison performed at block 228, that the likely current crack growth mechanism associated with the crack in the component being analyzed is an intergranular crack growth mechanism. At blocks 232 and 236, the computing system 100 generates a lifing prediction for the component based on the crack growth mechanism predicted at blocks 230, 234, respectively. At block 232, the computing system 100 uses transgranular lifing data to predict the cyclic life of the component. At block 236, the computing system 100 uses both transgranular lifing data and intergranular lifing data to make an end-of-life prediction for the component. The transgranular and intergranular lifing data may include, for example, the mechanism-based growth rate data 124. These life predictions can be generated using a commercially available life prediction tool, such as DARWIN or ZENCRACK. For example, life predictions can be obtained using computational software that employs basic fracture mechanics techniques to compare the growth rate (or material response) to a linear-elastic driving force. Such tools may employ more advanced structural assessments of the geometry with a simulated crack present or may employ planar simplifications to represent the geometry. Life predictions from either type of software assume that the analytical representation of the component includes a growth rate model that correctly represents the mechanism of growth. The blocks 222, 224, 226, 228, 230, 232, 234, 236 may, in some embodiments, be continually re-executed, e.g., as part of a real-time feedback control loop 238. For example, the loop 238 may execute each time a new set of component and mission parameters is received at block 210. To do this, the loop 238 may utilize the stored fracture maps 120 and modified DTT plots 122 to generate the predicted modified dwell transition temperature, the predicted crack growth mechanism, and the lifing prediction.

At block 240, the computing system 100 applies the component life prediction generated at block 232 or block 236 to one or more of: a component design process, a process of selecting a replacement part for the component, and a component maintenance planning or scheduling process. For example, the computing system 100 may supply the component life predictions generated at block 232 or block 236 to a component design module, a component material selection module, or a component maintenance planning module of the computing system 100, or to other computer applications or systems that provide component design, material selection, or maintenance planning functionality.

In the foregoing description, numerous specific details, examples, and scenarios are set forth in order to provide a more thorough understanding of the present disclosure. It will be appreciated, however, that embodiments of the disclosure may be practiced without such specific details. Further, such examples and scenarios are provided for illustration, and are not intended to limit the disclosure in any way. Those of ordinary skill in the art, with the included descriptions, should be able to implement appropriate functionality without undue experimentation.

References in the specification to "an embodiment," etc., indicate that the embodiment described may include a particular feature, structure, or characteristic, but every embodiment may not necessarily include the particular feature, structure, or characteristic. Such phrases are not necessarily referring to the same embodiment. Further, when a particular feature, structure, or characteristic is described in connection with an embodiment, it is believed to be within the knowledge of one skilled in the art to effect such feature, structure, or characteristic in connection with other embodiments whether or not explicitly indicated.

Embodiments in accordance with the disclosure may be implemented in hardware, firmware, software, or any combination thereof. Embodiments may also be implemented as instructions stored using one or more machine-readable media, which may be read and executed by one or more processors. A machine-readable medium may include any mechanism for storing or transmitting information in a form readable by a machine. For example, a machine-readable medium may include any suitable form of volatile or non-volatile memory.

Modules, data structures, and the like defined herein are defined as such for ease of discussion, and are not intended to imply that any specific implementation details are required. For example, any of the described modules and/or data structures may be combined or divided into sub-modules, sub-processes or other units of computer code or data as may be required by a particular design or implementation of the computing system 100.

In the drawings, specific arrangements or orderings of schematic elements may be shown for ease of description. However, the specific ordering or arrangement of such elements is not meant to imply that a particular order or sequence of processing, or separation of processes, is required in all embodiments. In general, schematic elements used to represent instruction blocks or modules may be implemented using any suitable form of machine-readable instruction, and each such instruction may be implemented using any suitable programming language, library, application programming interface (API), and/or other software development tools or frameworks. Similarly, schematic elements used to represent data or information may be implemented using any suitable electronic arrangement or data structure. Further, some connections, relationships or associations between elements may be simplified or not shown in the drawings so as not to obscure the disclosure.

This disclosure is to be considered as exemplary and not restrictive in character, and all changes and modifications that come within the spirit of the disclosure are desired to be protected.

The invention claimed is:

1. A computing system for assessing a manufactured metal alloy component for a turbine engine, the computing system comprising at least one computing device and instructions embodied in one or more non-transitory machine accessible storage media, the instructions executable by the at least one computing device to cause the computing system to:
   predict time-dependent crack growth behavior in a manufactured metal alloy component having a crack by:
   performing finite element modeling of the component;
   obtaining transition criteria from the finite element modeling;
   performing a fractographic evaluation of the crack in the component;
   creating a fracture mechanism map for the component based on the fractographic evaluation of a surface of the crack, the fracture mechanism map indicating operating conditions under which a transgranular crack growth mechanism is predicted to occur and operating conditions under which an intergranular crack growth mechanism is predicted to occur, wherein the operating conditions under which an intergranular crack growth mechanism is predicted to occur are different than the operating conditions under which a transgranular crack growth mechanism is predicted to occur; and
   determining, from the fracture mechanism map and the transition criteria, a modified dwell transition temperature for the component, the modified dwell transition temperature indicating a temperature at which the crack growth behavior of the component is predicted to transition from a transgranular crack growth mechanism to an intergranular crack growth mechanism;
   with the modified dwell transition temperature, generate a life prediction for the component; and modify one or more of: a design of the component, a material selection for the component, and a maintenance plan for the component, based on the life prediction.

2. The computing system of claim 1, wherein the instructions cause the computing system to obtain data indicating a mission temperature, wherein the mission temperature is a temperature to which the component is predicted to be subjected during operation of a turbine engine comprising the component, compare the mission temperature to the modified dwell transition temperature, and, based on the comparison of the mission temperature to the modified dwell transition temperature, predict the crack growth behavior of the crack in the component.

3. The computing system of claim 2, wherein the instructions cause the computing system to predict a cyclic life of the component using transgranular data if the crack growth mechanism is predicted to be transgranular.

4. The computing system of claim 3, wherein the instructions cause the computing system to predict a remaining life of the component using transgranular data and intergranular data if the crack growth mechanism is predicted to be intergranular.

5. The computing system of claim 1, wherein the transition criteria obtained from the finite element modeling are a function of one or more strain parameters.

6. The computing system of claim 5, wherein the one or more strain parameters comprise creep and elasticity.

7. The computing system of claim 1, wherein the instructions cause the computing system to obtain a plurality of mission-specific inputs relating to the component, wherein the mission-specific inputs comprise a mission temperature, a stress gradient, and a dwell period associated with the mission temperature and the stress gradient, and the instructions cause the computing system to determine the modified dwell transition temperature based on the stress gradient and the dwell period.

8. The computing system of claim 7, wherein the instructions cause the computing system to access a knowledge base of modified dwell transition temperature plots, select one of the modified dwell transition temperature plots based on the dwell period and the stress gradient, and use the selected modified dwell transition temperature plot to determine the modified dwell transition temperature.

9. The computing system of claim 1, wherein the instructions cause the computing system to apply a plurality of different levels of stress concentration to the component over time, fractographically evaluate the crack of the component at each of the different levels of stress concentration over time, develop a plurality of fracture mechanism maps based on the fractographic evaluation of the crack at the different levels of stress concentration over time, derive a plurality of modified dwell transition temperatures corresponding to each of the fracture mechanism maps, and determine the modified dwell transition temperature for the component by combining the derived modified dwell transition temperatures with one or more mission-specific inputs.

10. The computing system of claim 1, wherein the instructions cause the computing system to determine the modified dwell transition temperature by evaluating a geometry of the component.

11. The computing system of claim 10, wherein the geometry of the component comprises a notch, a fillet, and/or a hole.

12. The computing system of claim 1, wherein the fracture mechanism map corresponds to a stress gradient of the component, and the instructions cause the computing system to determine the modified dwell transition temperature based on the stress gradient of the component.

13. The computing system of claim 1, wherein the instructions cause the computing system to identify a strain parameter of the component from the finite element modeling, and use the identified strain parameter to determine the modified dwell transition temperature.

14. A computing system for predicting crack growth behavior in a metal alloy component, the computing system comprising:
  one or more computing devices; and
  instructions embodied in one or more non-transitory machine accessible storage media, the instructions executable by the one or more computing devices, the instructions comprising:
  a fracture map generator to cause the computing system to generate a plurality of fracture mechanism maps for the component, wherein each of the fracture mechanism maps indicates, for a different stress gradient, operating conditions under which a transgranular crack growth mechanism is predicted to occur and operating conditions under which an intergranular crack growth mechanism is predicted to occur, wherein the operating conditions under which an intergranular crack growth mechanism is predicted to occur are different than the operating conditions under which a transgranular crack growth mechanism is predicted to occur;
  a modified dwell transition temperature predictor to cause the computing system to determine a modified dwell transition temperature for the component from the plurality of fracture mechanism maps and a plurality of component-related inputs; and
  a component assessment system to assess the component for a turbine engine application based on the modified dwell transition temperature.

15. The computing system of claim 14, wherein the instructions comprise a crack growth mechanism predictor to cause the computing system to predict a crack growth mechanism of a crack in the component based on the modified dwell transition temperature.

16. The computing system of claim 14, wherein the crack growth mechanism predictor is to cause the computing system to compare the modified dwell transition temperature to a mission temperature, and wherein the mission temperature is a temperature to which the component is to be subjected during operation of a turbine engine comprising the component, and the crack growth mechanism predictor is to cause the computing system to predict the crack growth mechanism based on the comparison of the modified dwell transition temperature to the mission temperature.

17. The computing system of claim 14, wherein the instructions comprise a component life predictor to cause the computing system to predict a remaining life or a cyclic life of the component based on the predicted crack growth mechanism.

18. The computing system of claim 14, wherein the modified dwell transition temperature predictor is to cause the computing system to determine the modified dwell transition temperature based on a stress gradient associated with the component and a dwell period associated with the stress gradient and a mission temperature, and wherein the mission temperature is a temperature to which the component is to be subjected during operation of a turbine engine comprising the component.

19. The computing system of claim 14, wherein the modified dwell transition temperature predictor is to cause the computing system to determine the modified dwell transition temperature based on a plurality of strain parameters including creep and plasticity.

20. The computing system of claim 14, wherein the computing system comprises a finite element modeling subsystem to cause the computing system to perform finite element modeling of the component, and the computing system is to determines the modified dwell transition temperature based on transition criteria obtained as a result of the finite element modeling.

21. The computing system of claim 14, wherein the computing system comprises a scanning electron microscopy subsystem to cause the computing system to evaluate a fracture surface of the component, and the computing system generates the fracture mechanism maps based on the evaluation of the fracture surface of the component.

22. A computing system for predicting crack growth behavior in a metal alloy component of a turbine engine under a dwell condition, the computing system comprising instructions embodied in one or more non-transitory computer accessible storage media, the instructions executable by a processor to cause the computing system to:
- perform finite element modeling of the component;
- obtain, from the finite element modeling, a plurality of strain parameters;
- perform a fractographic evaluation of a fracture surface on the component;
- with data resulting from the fractographic evaluation, generate a time-dependent fracture mechanism map for the component, wherein the fracture mechanism map indicates, for a stress gradient associated with the component, operating conditions under which a transgranular crack growth mechanism is predicted to occur and operating conditions under which an intergranular crack growth mechanism is predicted to occur, wherein the operating conditions under which an intergranular crack growth mechanism is predicted to occur are different than the operating conditions under which a transgranular crack growth mechanism is predicted to occur;
- based on the fracture mechanism map, determine a modified dwell transition temperature for the component; and
- modify one or more of: a design, a material selection, and a maintenance plan for the component based on the modified dwell transition temperature.

23. The computing system of claim 22, wherein the instructions are executable by a processor to cause the computing system to predict a crack growth mechanism associated with the fracture surface of the component by evaluating the modified dwell transition temperature to a temperature to which the component may be subjected during the dwell condition of the turbine engine.

24. The computing system of claim 23, wherein the instructions are executable by a processor to cause the computing system to generate a life prediction for the component by evaluating data relating to the predicted crack growth mechanism.

* * * * *